United States Patent
Gavish et al.

(10) Patent No.: US 12,022,265 B2
(45) Date of Patent: *Jun. 25, 2024

(54) SYSTEM AND METHOD FOR PERSONALIZED FITTING OF HEARING AIDS

(71) Applicant: TUNED LTD., Gan Yoshiya (IL)

(72) Inventors: Omri Gavish, Gan Yoshiya (IL); Ron Ganot, Kfar Saba (IL)

(73) Assignee: TUNED LTD., Gan Yoshiya (IL)

(*) Notice: Subject to any disclaimer, the term of this patent is extended or adjusted under 35 U.S.C. 154(b) by 36 days.

This patent is subject to a terminal disclaimer.

(21) Appl. No.: 17/878,223

(22) Filed: Aug. 1, 2022

(65) Prior Publication Data
US 2023/0179934 A1    Jun. 8, 2023

Related U.S. Application Data

(63) Continuation of application No. 17/742,622, filed on May 12, 2022, which is a continuation of application No. 17/542,750, filed on Dec. 6, 2021, now Pat. No. 11,425,516.

(51) Int. Cl.
| | | |
|---|---|---|
| *H04R 25/00* | (2006.01) | |
| *A61B 5/12* | (2006.01) | |
| *G10L 17/00* | (2013.01) | |

(52) U.S. Cl.
CPC .......... *H04R 25/70* (2013.01); *A61B 5/123* (2013.01); *G10L 17/00* (2013.01); *H04R 25/505* (2013.01); *H04R 25/558* (2013.01); *H04R 2225/41* (2013.01); *H04R 2225/43* (2013.01); *H04R 2225/55* (2013.01)

(58) Field of Classification Search
CPC . A61B 2505/09; A61B 5/7203; A61B 5/7221; A61B 2560/0223; A61B 2560/0242; A61B 2560/0431; A61B 5/123; H04R 25/70; H04R 5/123; H04R 25/505; H04R 25/558; H04R 2225/41; H04R 2225/43; H04R 2225/55; G10L 17/00
See application file for complete search history.

(56) References Cited

U.S. PATENT DOCUMENTS

| | | | |
|---|---|---|---|
| 9,532,152 B2 | 12/2016 | Shennib | |
| 9,782,131 B2* | 10/2017 | Van Hasselt | G16H 40/67 |
| 10,757,513 B1 | 8/2020 | Chen et al. | |
| 2013/0178162 A1 | 7/2013 | Neumeyer et al. | |
| 2013/0243227 A1 | 9/2013 | Kinsberger et al. | |
| 2014/0169574 A1 | 6/2014 | Choi et al. | |
| 2014/0211973 A1 | 7/2014 | Wang et al. | |
| 2014/0309549 A1* | 10/2014 | Selig | A61B 5/123 |
| | | | 600/559 |
| 2015/0271607 A1 | 9/2015 | Sabin | |
| 2016/0309267 A1 | 10/2016 | Fitz et al. | |
| 2017/0201839 A1 | 7/2017 | Manchester | |

(Continued)

FOREIGN PATENT DOCUMENTS

| | | |
|---|---|---|
| CN | 109151692 A | 1/2019 |
| EP | 3614695 A1 | 2/2020 |

*Primary Examiner* — Brian Ensey
(74) *Attorney, Agent, or Firm* — The Roy Gross Law Firm, LLC; Roy Gross

(57) ABSTRACT

Disclosed are system and methods for automated fitting of a hearing aid, through an automated hearing test based upon which a suitable set of hearing aid parameters is determined.

17 Claims, 12 Drawing Sheets

(56) References Cited

U.S. PATENT DOCUMENTS

| | | |
|---|---|---|
| 2017/0230762 A1 | 8/2017 | Simonides et al. |
| 2018/0108370 A1 | 4/2018 | Dow et al. |
| 2018/0115841 A1 | 4/2018 | Apfel et al. |
| 2018/0213339 A1 | 7/2018 | Shah et al. |
| 2018/0227682 A1 | 8/2018 | Lederman |
| 2019/0046794 A1 | 2/2019 | Goodall et al. |
| 2019/0082274 A1 | 3/2019 | Dickmann et al. |
| 2019/0166435 A1 | 5/2019 | Crow et al. |
| 2019/0182606 A1 | 6/2019 | Peterson et al. |
| 2019/0356989 A1* | 11/2019 | Li ................... A61B 5/121 |
| 2020/0322742 A1 | 10/2020 | Boretzki et al. |
| 2020/0389743 A1 | 12/2020 | Li et al. |
| 2020/0404431 A1 | 12/2020 | Jung et al. |

\* cited by examiner

Step 520
Put on manual

Step 530
Device ear check

SYSTEM AND METHOD FOR PERSONALIZED FITTING OF HEARING AIDS

CROSS REFERENCE TO RELATED APPLICATIONS

This application is a continuation of U.S. patent application Ser. No. 17/742,622 filed on May 12, 2022, which is a continuation of U.S. patent application Ser. No. 17/542,750 filed on Dec. 6, 2021, the contents of which are all incorporated herein by reference in their entirety.

TECHNICAL FIELD

The present disclosure relates generally to the field of personalized fitting of hearing solutions, specifically adjustments executable by a user of the hearing aid, using artificial intelligence.

BACKGROUND

Modern hearing aids are today most often controlled by digital data processors and signal processors.

However, typically programming and adjusting of parameters of the hearing aid requires a user to make an appointment with a hearing professional (typically an audiologist) and to come into an office that has the necessary equipment. This imposes the inconvenience, expense and time consumption associated with travel to a remote location, which is particularly problematic for users with limited mobility, users who live in remote areas, and/or users who live in developing countries where a hearing professional may not be available.

There therefore remains a need for systems and methods that enable a user to autonomously adjust parameters of his/her hearing aid, as per his/her own hearing experience and at a time of his/her need.

SUMMARY

Aspects of the disclosure, according to some embodiments thereof, relate to systems, platforms and methods that enable a user to autonomously fit the parameters to a hearing aid of his choice so as to obtain a best possible hearing experience.

Advantageously the fitting can be adjusted based on whether or not the user is in possession of a hearing device. That is, the hearing test made as a part of the fitting process may be adjusted to be conducted on headphones in case the subject is not in possession of a hearing aid, as e.g. in the case of a user who is only considering to acquire a hearing aid or in the process of doing so. Similarly, in case the user is already in possession of the hearing aid, hearing aid specific adjustment may be made, such as an automatic switching of an operation mode of the hearing aid from a hearing mode to a test mode, or such as taking into account the brand of the hearing aid, requesting use of a particular dome etc., all adjustment configured to ensure the highest possible quality of the hearing test and subsequent setting of suitable hearing parameters.

Moreover, a microphone positioned, for example, on the user's mobile device, may be utilized to record environmental sounds. This may serve to record background noise at the frequencies transmitted to the user during the hearing test and subsequently be used to increase the quality of the test results. Moreover, the microphone may be further used to determine the degree of leakage of the sound transmitted to the hearing aid or headphones, which leakage should be deducted from the intensity of the signal transmitted or otherwise be taken into account, when transforming the hearing test into hearing aid parameters.

As a further advantage, the fitting can be made at a time and place of the user's convenience.

According to some embodiments, there is provided a method of automated fitting of a hearing aid, the method comprising: conducting a hearing test comprising: changing a mode of the hearing aid from a hearing mode to a test mode, wherein the test mode is configured to minimize penetration of external sounds into the hearing aid; utilizing or requesting to utilize a microphone to record environmental sounds; providing puretone sounds at different frequencies, requesting from the user a feedback regarding the quality of the sounds at each of the different frequencies; and determining a suitable set of hearing aid parameters for the hearing aid, based on the feedback and the recorded environmental sounds and optionally further on the type of hearing device utilized for the test and/or the brand of the hearing aid.

According to some embodiments, the method further comprises providing or obtaining an indication regarding the type of hearing device utilized for the hearing test, wherein in case the user is not in possession of a hearing aid, the method comprises requesting the user to utilize headphones, wherein the requesting of the user to utilize headphones comprises requesting the user to provide at least one feature of the headphone, wherein the at least one feature is selected from: closed/open back, on-ear/over-ear/in ear/ear-buds, wired/wireless, noise-cancelling, brand or any combination thereof.

According to some embodiments, the method further comprises a step of uploading the feedback to a cloud, wherein the determining of the suitable set of hearing aid parameters for the hearing aid is performed at the cloud. According to some embodiments, the method further comprises a step of downloading the suitable set of hearing aid parameters to the subject's mobile and/or hearing aid.

According to some embodiments, the method further comprises providing the user with an indication that the hearing test cannot be reliably executed, when the environmental sounds recorded reach a predetermined threshold level.

According to some embodiments, when the user is in possession of the hearing aid, the method comprises providing a request to the user to utilize a hearing aid dome, the dome configured to seal off external sounds and/or minimize leakage of sounds transmitted through the hearing aid to the environment.

According to some embodiments, the determining of the suitable set of hearing aid parameters comprises normalizing the feedback obtained, based on the environmental sounds recorded at each of the different frequencies.

According to some embodiments, the hearing test may be executed via the internet or using a dedicated mobile app. According to some embodiments, when the hearing test is executed using the internet, the method further comprises requesting the user to indicate which internet browser is being used or automatically identifying the internet browser used. According to some embodiments, the method further comprises normalizing the feedback obtained, based on the internet browser used.

According to some embodiments, when the hearing test is executed using the dedicated mobile app, the possession of the hearing aid may be automatically identified. According to some embodiments, four scenarios of device identification may be envisaged: 1) No device is located, in which case the user may be requested to either confirm that he/she is not in possession of a device or to turn on/properly activate the device (optionally followed by visual instruction); 2) Only one device is located, in which case the user may be requested to confirm that indeed he/she is only in possession of a single hearing aid (or optionally the user may be requested to activate second device), 3) Two hearing devices are identified, in which case the user may automatically be transferred to the next step (e.g. instructions to put on his/her hearing aid); 4) More than two device are located, in which case the method may include automatic sorting of the devices, for example, according to signal strength, and a pair of hearing aids be suggested to the user.

According to some embodiments, when the user is in possession of the hearing aid and the hearing test is performed using the dedicated mobile app, the method further comprises automatically changing a mode of the hearing aid from a test mode to a hearing mode, if a call enters during the hearing test.

According to some embodiments, the determining of the suitable set of hearing aid parameters comprises obtaining an external set of recommended hearing aid parameters, and adjusting the external set of recommended hearing aid parameters, based on the hearing test.

According to some embodiments, the determining of the suitable set of hearing aid parameters comprises obtaining an initial set of recommended hearing aid parameters, the initial set of hearing aid parameters being hearing aid parameters obtained from a subject having a similar user profile. According to some embodiments, the user profile is determined based on at least two parameters selected from age, gender, years of hearing deficiency, source of hearing deficiency, previous hearing aid usage, interests/hobbies, occupation. According to some embodiments, the similar user profile is chosen by the user.

According to some embodiments, the hearing test further comprises providing to the subject one or more recordings of speech of one or more individuals with whom the user has frequent interactions and wherein the determining of the suitable set of hearing aid parameters comprises providing a set of parameters optimized for hearing the speech of the one or more individuals with whom the user has frequent interactions. According to some embodiments, the method further comprises automatically recognizing speech of the one or more individuals with whom the user has frequent interactions and utilizing the set of parameters optimized for hearing the speech of the one or more individuals with whom the user has frequent interactions.

According to some embodiments, there is provided a system for personalized hearing test and hearing aid adjustment, the system comprising a processing logic configured to: change a mode of the hearing aid from a hearing mode to a test mode, wherein the test mode is configured to minimize penetration of external sounds into the hearing aid; utilize or requesting to utilize a microphone to record environmental sounds; provide puretone sounds at different frequencies to the user, request from the user a feedback regarding the quality of the sounds at each of the different frequencies; and determine a suitable set of hearing aid parameters for the hearing aid, based on the feedback and the recorded environmental sounds and the type of hearing device utilized for the test or brand of the hearing aid.

According to some embodiments, the system further comprises providing or obtaining an indication regarding the type of hearing device utilized for the hearing test, wherein in case the user is not in possession of a hearing aid, the control logic is configured to trigger a request to the user to utilize headphones, wherein the requesting of the user to utilize headphones comprises requesting the user to provide at least one feature of the headphone, wherein the at least one feature is selected from: closed/open back, on-ear/over-ear/in ear/ear-buds, wired/wireless, noise-cancelling, brand or any combination thereof.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not drawn to scale. Moreover, two different objects in the same figure may be drawn to different scales. In particular, the scale of some objects may be greatly exaggerated as compared to other objects in the same figure.

In block diagrams and flowcharts, certain steps may be conducted in the indicated order only, while others may be conducted before a previous step, after a subsequent step or simultaneously with another step. Such changes to the orders of the step will be evident for the skilled artisan. Chat bot conversations are indicated in balloons and user instructions provided through selecting an icon or an option from a scroll down menu is indicated by grey boxes. It is understood that combining both text conversations and buttons is optional, and that the entire conversation tree may be through text messages or even, but generally less preferred, through instruction buttons and/or scroll-down menus.

DETAILED DESCRIPTION

Figure 1:
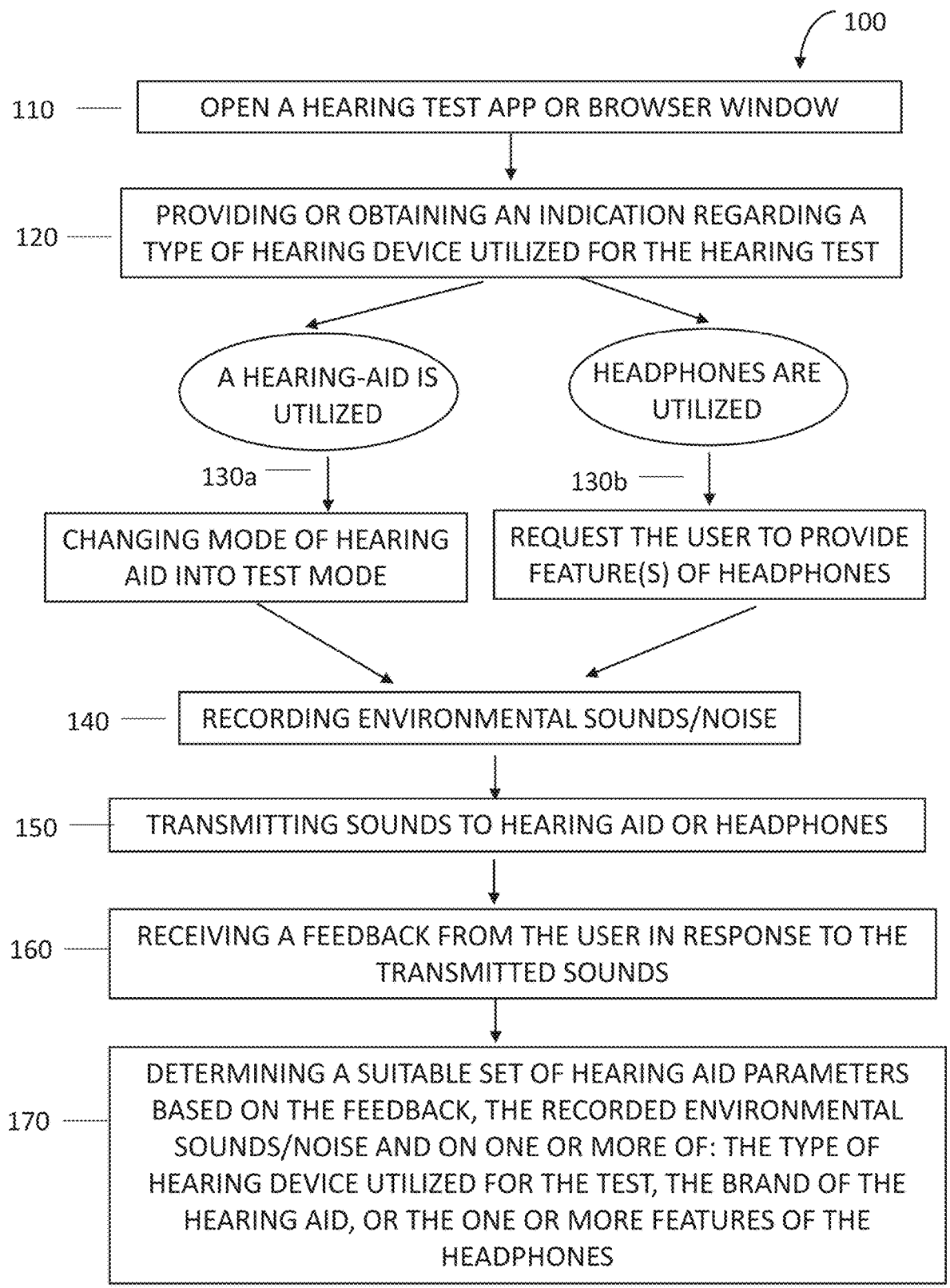
FIG. 1 is a flowchart of the herein disclosed method for automated fitting of a hearing aid, according to some embodiments.

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

According to some embodiments, there is provided a method for automated fitting of a hearing aid, the method comprising: conducting a hearing test which includes providing or obtaining an indication regarding the type of hearing device utilized for the hearing test (hearing aid or headphones), transmitting sounds at different frequencies to the hearing aid or to the headphones, requesting from the user a feedback regarding the quality of the sounds at each of the different frequencies; and determining a suitable set of hearing aid parameters for the hearing aid, by applying an algorithm on the feedback and on one or more of: the type of hearing device utilized for the test, recorded environmental sounds, and the one or more features of the headphones.

According to some embodiments, the algorithm is an artificial intelligence (AI) algorithm. According to some embodiments, the algorithm is a machine learning algorithm. According to some embodiments, the machine learning algorithm is a supervised learning algorithms built on a mathematical model of a set of training data in which the output is that of an audiologist.

According to some embodiments, the supervised learning algorithms may include active learning, classification and regression.

As used herein, the term "hearing test" refers to an evaluation of the sensitivity of a person's sense of hearing. The standard and most common type of hearing test is pure tone audiometry, which measures the air and bone conduction thresholds for each ear in a set of 8 standard frequencies from 250 Hz to 8000 Hz. The result of the test is an audiogram diagram which plots a person's hearing sensitivity at the tested frequencies.

According to some embodiments, if the result of the hearing test indicates a higher than predetermined difference such as, but not limited to, more than 10 db or more than 15 db between left and right ears, the method will issue a query to the user as to whether he/she is aware of such difference. In case the user is unaware of such hearing difference between the ears, the method may include issuing a notification to the user that an audiologist and/or ear doctor is to be contacted. This since a discrepancy in the hearing may be indicative of a medical issue such, as but not limited to, cerumen (wax) in the ear canal, bone growth, growth on the vestibular nerve, head injury, infection (sudden deafness—which often affects only one ear—should be considered a medical emergency)

According to some embodiments, when the user is in possession of a hearing aid, the method comprises changing the mode of the hearing aid from a hearing mode to a test mode, wherein the test mode is configured to minimize penetration of external sounds into the hearing aid.

According to some embodiments, the method further comprises utilizing or requesting to utilize a microphone (which may, for example, be positioned on a mobile device of the user) to record environmental sounds (noise). According to some embodiments, the environmental sounds (noise) may be recorded separately for each frequency band, such as, but not limited to, specifically one or more of the following frequency bands: 250 MHz, 500 Mhz, 1 k, 2 k, 4 k, and 6 K. Each possibility is a separate embodiment.

According to some embodiments, the determining of the suitable set of hearing aid parameters includes normalizing the feedback obtained from the user, based on the environmental sounds/noise recorded at each of the different frequencies. According to some embodiments, the method further includes providing the user with an indication that the hearing test cannot be reliably executed, when the environmental sounds/noise recorded reach a predetermined threshold level. According to some embodiments, the method further includes displaying (e.g. graphically) the level of environmental sounds/noise recorded before and/or during the performing of the hearing test.

According to some embodiments, the microphone may record sounds resulting from leakage of sounds transmitted to the user, in which case the actual sound level reaching the user is lower than that transmitted, thus negatively influencing the results of the hearing test. According to some embodiments, when leakage is determined, the test may either be repeated and/or the test results adjusted, based on the intensity of the leakage. According to some embodiments, an indication/suggestion may be provided to the user, e.g. via the user interface, to go to a more quiet sound environment. According to some embodiments, the user may be requested, e.g. via the user interface, to insert the dome deeper inside the ear canal or to replace the dome of the hearing aid. According to some embodiments, the adjustment may include multiplying the test result by a factor indicative of the intensity of the leakage. According to some embodiments, the adjustment may include subtracting the intensity of the leakage from the intensity of the input signal.

According to some embodiments, when the user is not in possession of a hearing aid, the method may include requesting, e.g., through a user interface, the user to utilize headphones. According to some embodiments, the method further includes requesting, e.g., via the user interface, to provide at least one feature of the headphone. According to some embodiments, the at least one feature is selected from: closed/open back, on-ear/over-ear/ear-buds/in-ear ear buds, wired/wireless headphones, noise-cancelling headphones, head phone brand or any combination thereof. Each possibility is a separate embodiment.

As used herein, the term "headphones" refer to a pair of small loudspeaker drivers worn on or around the head over a user's ears. They are electroacoustic transducers, which convert an electrical signal to a corresponding sound.

As used herein the term "closed-back headphones" refer to headphones that are completely sealed around the back, thereby only allowing sound out where it can reach a user's ear. Closed-back headphones normally block out a lot more outside noise, yielding better sound isolation.

As used herein the term "open-back headphones" refer to headphones that allow air to pass through the ear cups from the rear of the speaker. This lessens resonances and low-frequency build-up caused by rear enclosure. Open-ended headphones typically provide/ensure natural and clear sounds.

As used herein the term "over-ear headphones" refer to headphones with headbands and large ear cups that fully encompass the ears of its user.

As used herein the term "on-ear headphones" refer to headphones with headbands and with more compact ear cups than over-ear headphones. The ear cups typically rest on the ears of its user.

As used herein the term "ear-buds" refer to ultra-portable headphones with earbud tips, that rest at the edge of the ear canal. Ear-buds are typically devoid of headbands.

As used herein the term "in-ear buds" ultra-portable with small earbud tips, which are inserted into the ear canal. In-ear ear-buds are typically devoid of headbands and ear-bud tips.

It was surprisingly found that the hearing level (sound) transmitted through headphones may vary for different types of headphones. Accordingly, based on the type of headphones utilized, a different sound signal may be transmitted so as to calibrate the hearing test for different headphones.

According to some embodiments, when the user is in possession of the hearing aid, the method further includes providing a request to the user (e.g. via a sound message to the hearing aid or through an App associated therewith) to utilize a hearing aid dome configured for performing a hearing test. According to some embodiments, the hearing aid dome requested to be utilized may be configured to seal-off external sounds and/or minimize leakage of sounds transmitted through the hearing aid to the environment.

As used herein, the term "hearing aid," refers to all types of hearing enhancement devices, including medical devices prescribed for the hearing impaired, and personal sound amplification products (PSAP) generally not requiring a prescription or a medical waiver. The device type or "style" may be any of invisible in the canal (ITC), in-the-canal (ITC), in the ear (ITE), a receiver in the canal (RIC), or behind the ear (BTE). A canal hearing device refers herein to any device partially or fully inserted in the ear canal.

According to some embodiments, the method further includes a step of uploading the feedback to a cloud, wherein the determining of the suitable set of hearing aid parameters for the hearing aid is performed in the cloud. It is understood that the "in-cloud" determining of the parameters significantly reduces the computational load required, which may be of significance in the elderly population who often is in possession of older computational devices (whether PCs or smartphones). According to some embodiments, the cloud server is generating hearing aid settings and programs according to the specified audiogram, age and gender of the user, while also considering if the user is an experienced hearing aid user or not. According to some embodiments, the generating of the hearing settings and programs may further include posing to the user one or more questions, such as "how old is the youngest child in your family?" or "which music do you prefer to listen to?" and the like, thereby further improving the prediction of the most suitable settings/fitting for the specific user.

After calculating initial fitting parameters, additional adjustments may be applied to the hearing aid settings/programs depending on particular hearing aid model, tubing and dome. According to some embodiments, depending on the type of headphones utilized, the hearing test will adjust the output volume of speech and/or puretone sounds in order to compensate for the known difference. According to some embodiments, the method further includes a step of downloading the suitable set of hearing aid parameters to the subject's mobile phone and/or hearing aid.

According to some embodiments, the suitable set of parameters determined are applied to the hearing aid via BLE. According to some embodiments, the suitable set of parameters may include more than one set of parameters. According to some embodiments, a first set of parameters may initially be provided. Typically, the first set of parameters is suboptimal but suitable at an initial stage while the user is getting used to using a hearing aid. According to some embodiments, one or more (e.g. 1, 2, 3, 4 or more) intermediate set of parameters may be provided, in order to gradually accustom/acclimatize the user to a last set of parameters, also referred to as an optimal set of parameters, which is the set of parameters which are most suitable to the user's hearing deficiency. According to some embodiments, the first, intermediate, and last set of parameters may be automatically implemented, e.g. at certain time intervals after initiation of use of the hearing aid. According to some embodiments, the first, intermediate, and last set of parameters may be implemented, after recurring hearing tests. According to some embodiments, the first, intermediate and last sets of parameters of the acclimatization process are obtained by applying an acclimatization algorithm on the suitable set of parameters determined based on the hearing test or by applying the acclimatization algorithm directly on the feedback and on the one or more of: the type of hearing device utilized for the test, recorded environmental sounds, and the one or more features of the headphones. Each possibility is a separate embodiment. According to some embodiments, the last set of parameters may be the set of suitable parameters determined based on the hearing test (i.e. based on the feedback and the on one or more of: the type of hearing device utilized for the test, recorded environmental sounds, and the one or more features of the headphones).

According to some embodiments, the hearing test may be executed via the internet or using a dedicated mobile app. It was surprisingly found that the same sound signal output may differ when transmitted through the internet than through a mobile app. Similarly, the signals received may differ depending on the internet browser utilized. Therefore, if the internet is used for the test, the method may further include requesting the user to indicate which internet browser is being used. Alternatively, the identification of whether an App or the internet is used for the test, and if the internet, which browser may be automatically identified. According to some embodiments, the feedback obtained from the user, in response to the transmitting of the sound signals, may be normalized based on whether an App or the internet is used for the test, and if the latter, which internet browser. According to some embodiments, depending on the user's operating system, the hearing test will adjust the output volume of speech and/or puretone sounds in order to compensate known difference between the operating systems and their sound transmission.

According to some embodiments, when the hearing test is executed using a dedicated mobile app, the possession of the hearing aid may be automatically identified without requiring a user-indication.

According to some embodiments, when the user is in possession of the hearing aid and the hearing test is performed using the dedicated mobile app, the method may further include automatically changing a mode of the hearing aid from the test mode to a hearing mode, if a call enters during the hearing test. In addition, the method may further include automatically changing the mode of the hearing aid from the hearing mode back to the test mode, upon completion of the call.

According to some embodiments, the method may further include automatically changing the mode of the hearing aid from the test mode to a hearing mode if the user leaves the hearing test App during the hearing test. In addition, the method may further include automatically changing the mode of the hearing aid from the hearing mode back to the test mode, upon return to the App.

According to some embodiments, determining the suitable set of hearing aid parameters may include obtaining an external set of recommended hearing aid parameters (e.g. based on a prior hearing test) and optionally adjusting the external set of recommended hearing aid parameters, based on the hearing test/the method disclosed herein. According to some embodiments, the external parameters may include user profile information such as, but not limited to, gender, age, hearing aid experience, —language type (tonal or non-tonal), hearing aid model (for applying additional post processing suitable to the particular model, manually inserted audiograms (optionally including both air conduction values and bone conduction values from printed audiograms for improved accuracy).

According to some embodiments, the determining of the suitable set of hearing aid parameters may include obtaining an initial set of recommended hearing aid parameters, the initial set of hearing aid parameters being hearing aid parameters obtained from a subject having a similar user profile. In such case the hearing test will be used to adjust the initial set of recommended hearing aid parameters using the herein disclosed method. According to some embodiments, the user may choose a user profile that he/she finds particularly suitable. For example, the user may choose a profile of a user having a same age and/or a same underlying cause of hearing deficiency, and/or a same hobby (e.g., listening to classical music or playing cards with friends) etc. based upon which the hearing test may be performed, thereby ensuring a best possible baseline for the hearing test and/or for the setting of optimal hearing aid parameters. According to some embodiments, the user profile is determined based on at least two parameters selected from age, gender, years of hearing deficiency, source of hearing deficiency, previous hearing aid usage, interests/hobbies, occupation, or any combination thereof. Each possibility is a separate embodiment.

According to some embodiments, the method further includes recording the speech of one or more individuals with whom the user has frequent interactions, such as, but not limited to, a family member, a relative, a friend, a co-worker, a nurse, an aid or the like. According to some embodiments, recording a speech may include recording sentences. According to some embodiments, recording a speech may include recording just a few words whereafter an algorithm generates sentences spoken with an essentially identical voice, using voice cloning technologies, as essentially known in the art.

According to some embodiments, the hearing test further comprises transmitting to the user one or more sentences, whether direct recordings of the sentences or computer-generated sentences constructed from recordings. According to some embodiments, the determining of the suitable set of hearing aid parameters may further include providing determining a set of parameters optimized for hearing the voice of the individuals with whom the user has frequent interactions. According to some embodiments, the method may further include applying an algorithm configured to recognize the voice of the one or more individuals with whom the user has frequent interactions and to automatically utilize the set of parameters optimized for hearing the voice of the one or more individuals with whom the user has frequent interactions.

According to some embodiments, the method further includes recording changes to the hearing aid settings made after the fitting of the suitable set of hearing aid parameters. According to some embodiments, the recorded changes may be used to create an updated and personalized fitting algorithm which the user can utilize for future fittings. According to some embodiments, the recorded changes may be used to update the fitting algorithm in general or for a subset of users (e.g. users who frequently listen to classical music). According to some embodiments, the algorithm may be updated based on user changes made at each stage of the acclimatization process, According to some embodiments, changes made during acclimatization process may be used to improve/update the acclimatization algorithm and/or to adjust the last set of parameters determined according to the hearing test.

According to some embodiments, there is provided a system for personalized hearing test and hearing aid adjustment, the system comprising a processing logic configured to: obtain an indication regarding the type of hearing device utilized for a hearing test, trigger the providing of sounds at different frequencies to the hearing aid or to the headphones; trigger a request to the user to provide a feedback regarding the quality of the sounds at each of the different frequencies; and determine a suitable set of hearing aid parameters for the hearing aid, based on the feedback and on one or more of: the type of hearing device utilized for the test, the one or more features of the headphones and recorded environmental sounds.

According to some embodiments, the processing logic may be further configured to utilize or to request utilizing a microphone positioned on a mobile device of the consumer to record environmental sounds.

According to some embodiments, the at least one feature is selected from: closed/open back, on-ear/over-ear/in ear/ear-buds, wired/wireless, noise-cancelling, brand or any combination thereof. Each possibility is a separate embodiment.

According to some embodiments, in a case where the user is in possession of the hearing aid, the control logic is configured to trigger a change in a mode of the hearing aid from a hearing mode to a test mode, wherein the test mode is configured to minimize penetration of external sounds into the hearing aid.

According to some embodiments, in a case where the user is not in possession of a hearing aid, the control logic is configured to trigger a request to the user to utilize headphones, wherein the requesting of the user to utilize headphones comprises requesting the user to provide at least one feature of the headphone.

In the description and claims of the application, the words "include" and "have", and forms thereof, are not limited to members in a list with which the words may be associated.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods according to some embodiments may be described in a specific sequence, methods of the disclosure may include some or all of the described stages carried out in a different order. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

Reference is now made to FIG. 1, which is a flow chart 100 of the herein disclosed method for personalized hearing aid adjustment. It is understood to one of ordinary skill in the art that while the steps are shown as sequential, the order of at least some of the steps may be changed and/or be conducted simultaneously. Those skilled in the art will readily understand which are such steps.

In step 110 of the method, an app or internet browser window for conducting a hearing test is opened. Then, in step 120 the device utilized for the hearing test is identified. The identification may be automatic identification. For example, if an App is utilized, the App may be configured to automatically identify a user's hearing aid, if available. Alternatively, the identification may include requesting and receiving an input from the user regarding the type of device utilized.

If a hearing aid is used, the next step, may be step 130a in which the mode of the hearing aid is automatically changed to a hearing mode. If headphones are used, the user may in step 130b be requested to provide one or more features of the headphones such as, but not limited to, whether the headphones are closed or open back headphones, on-ear, over-ear, in ear or ear-buds, wired or wireless, noise-cancelling or not, brand or the like.

Moreover, in step 140, environmental sounds may be recorded e.g. by utilizing (optionally upon request) a microphone of the user's mobile device, computer and/or hearing aid. If the sound levels of the environment are not detrimental to the conducting of the hearing test, the next step of the method is the hearing test itself, which includes providing sounds at different frequencies to the hearing aid or to the headphones (step 150) and requesting the user's response thereto (step 160).

Lastly, in step 170 a suitable set of hearing aid parameters may be determined based on the feedback of the user to the transmitted sounds, the recorded environmental sounds/noise and on one or more of: the type of hearing device utilized for the test, a brand of the hearing aid, or the one or more features of the headphones.

Figure 2:
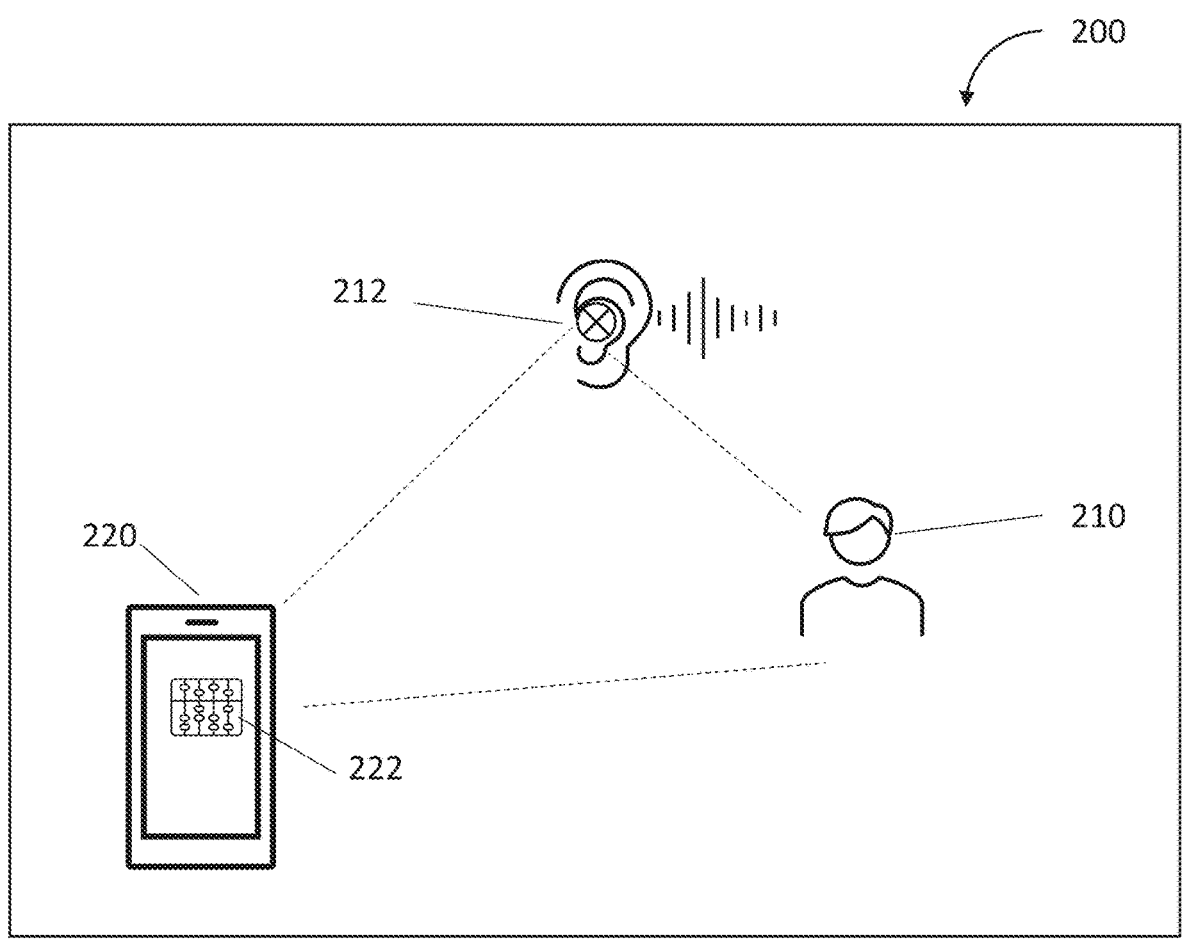
FIG. 2 schematically illustrates a system for automated fitting of a hearing aid, using a hearing aid according to some embodiments.

Reference is now made to FIG. 2, which is a schematic illustration of a system 200 for automated fitting of a hearing aid, according to some embodiments. System 200 includes a hearing aid 212 of a user 210, at least one hardware processor, here the user's mobile phone 220 including a non-transitory computer-readable storage medium having stored thereon program code, the program code executable by the hardware processor, here mobile app 222 configured to execute the method as essentially outlined in flowchart 100, while receiving input and/or instructions (such as a user-initiated input).

Figure 3:
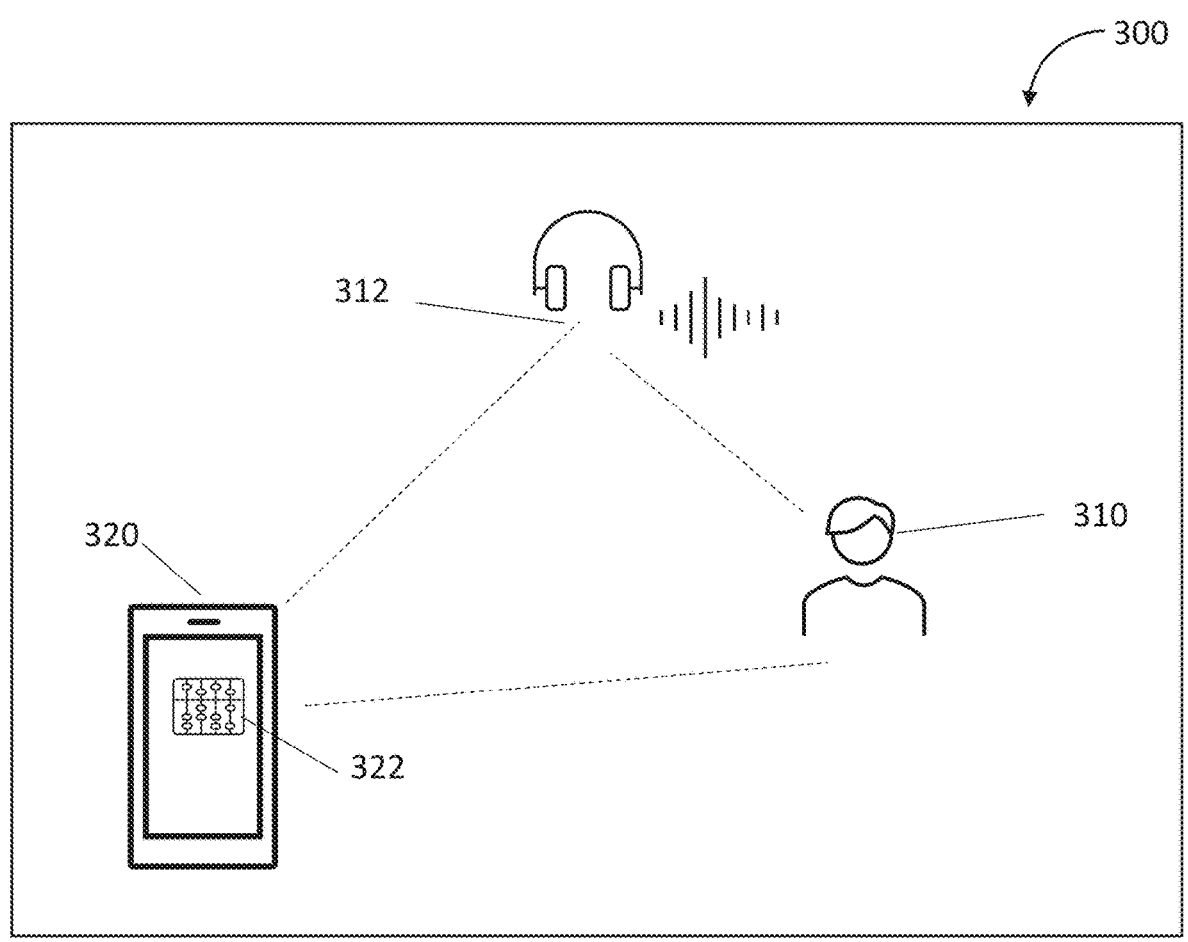
FIG. 3 schematically illustrates a system for automated fitting of a hearing aid, using headphones according to some embodiments.

Reference is now made to FIG. 3, which is a schematic illustration of a system 300 for automated fitting of a hearing aid, according to some embodiments. System 300 includes headphones 312 of a user 310, at least one hardware processor, here the user's mobile phone 320 including a non-transitory computer-readable storage medium having stored thereon program code, the program code executable by the hardware processor, here mobile app 322 configured to execute the method as essentially outlined in flowchart 100, while receiving input and/or instructions (such as a user-initiated input).

Figure 4:
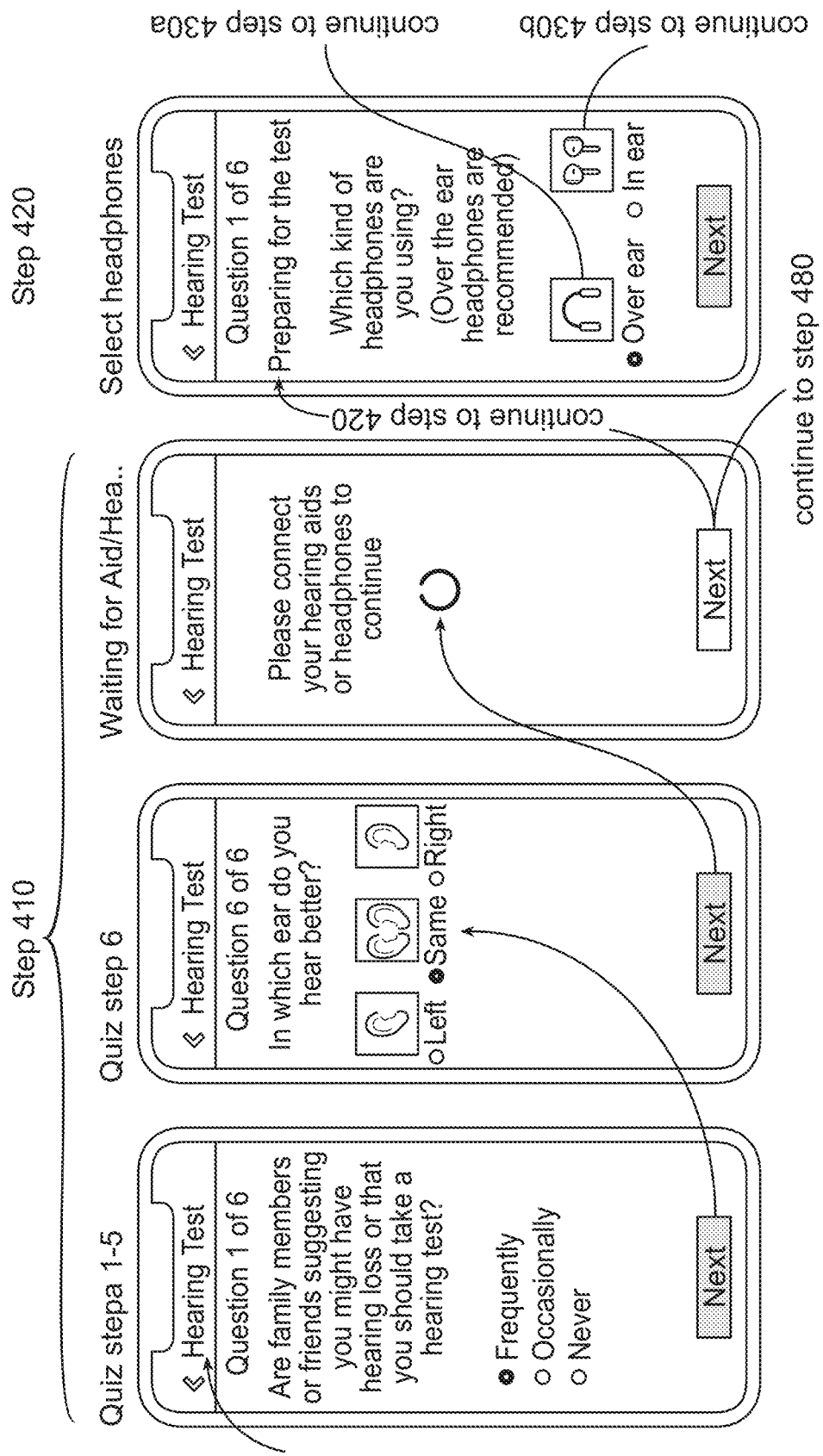
FIG. 4 schematically illustrates the flow of the herein disclosed method for automated fitting of a hearing aid, executed using a mobile App, according to some embodiments.
Figure 4:
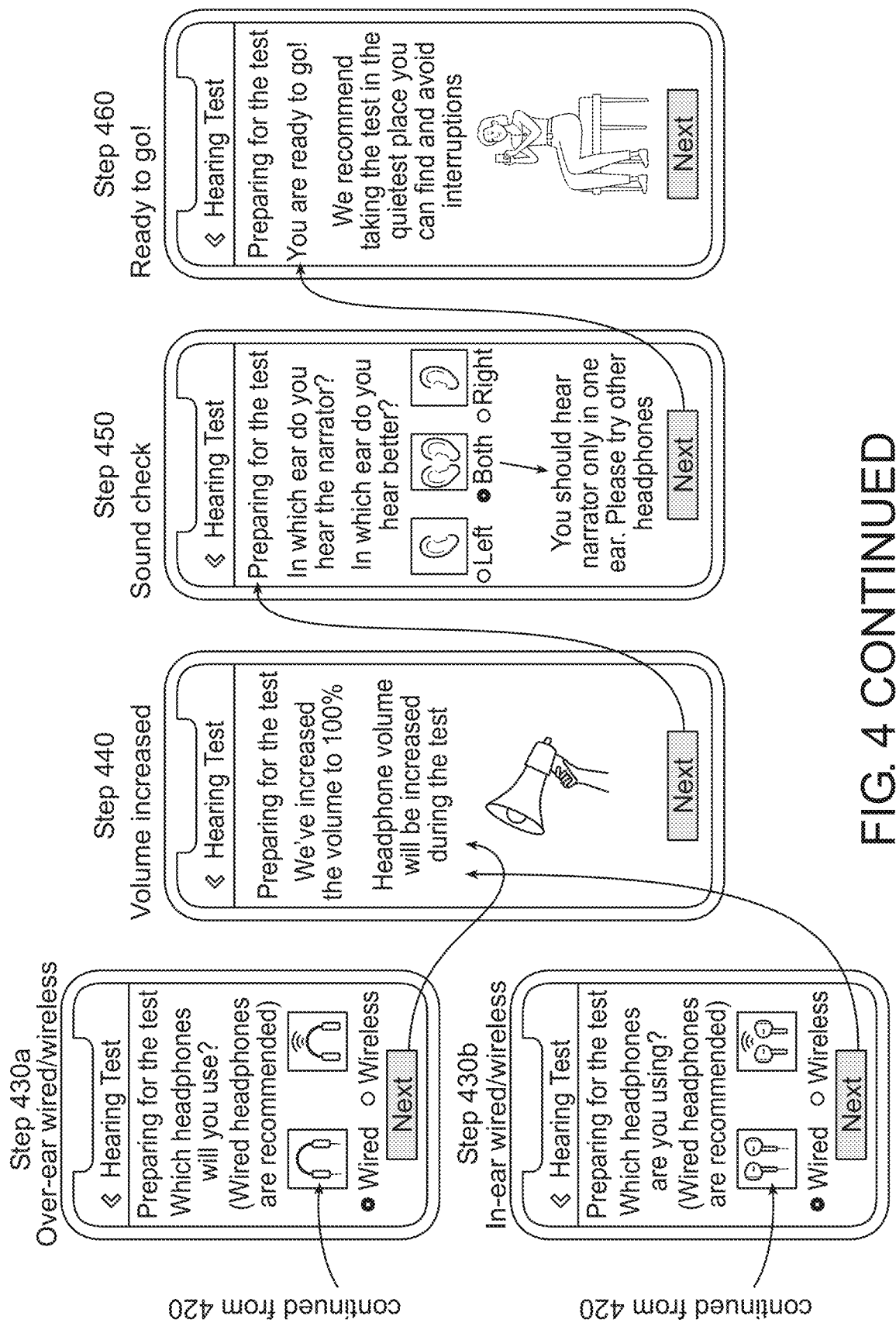
Figure 4:
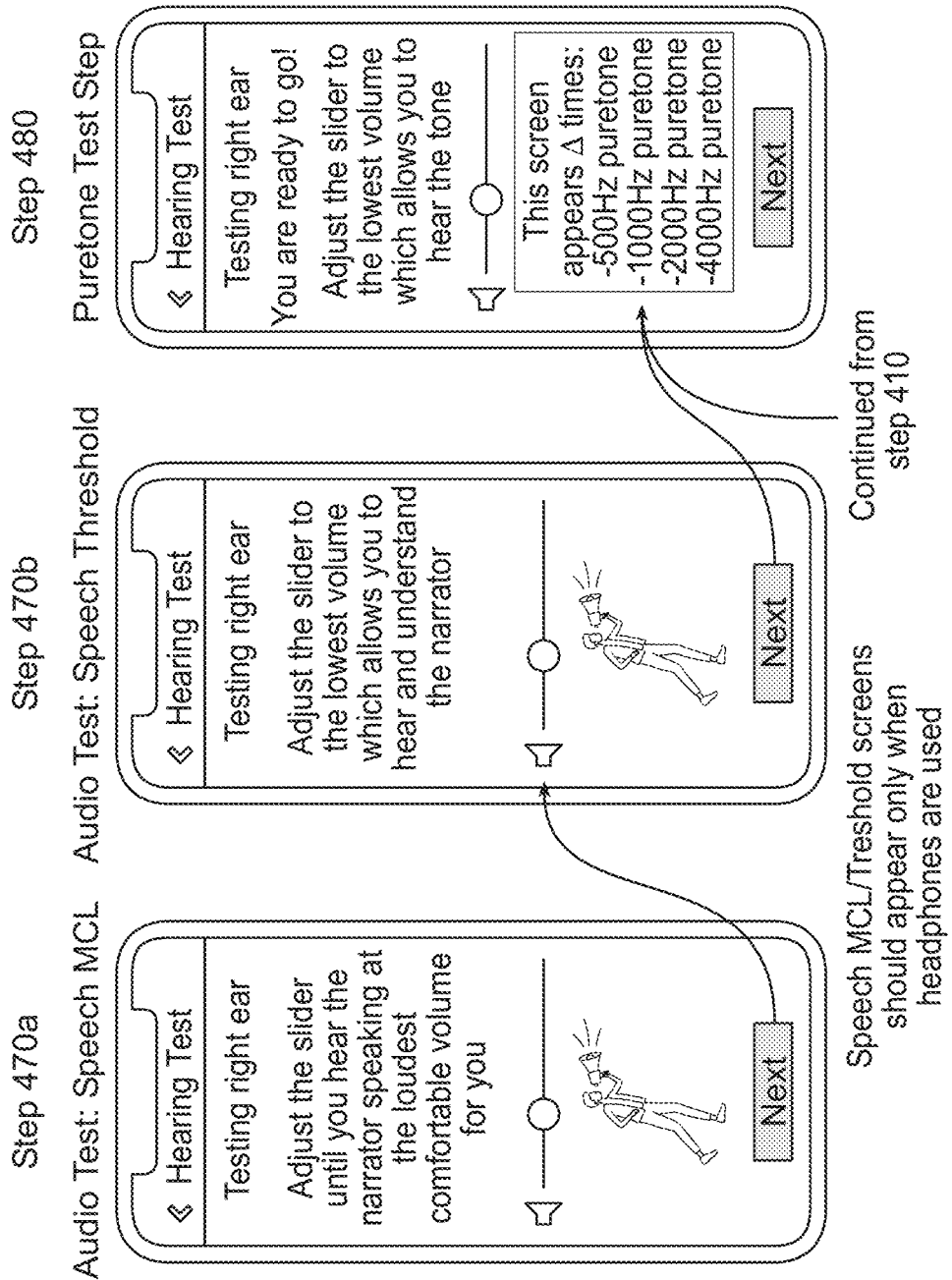
Figure 4:
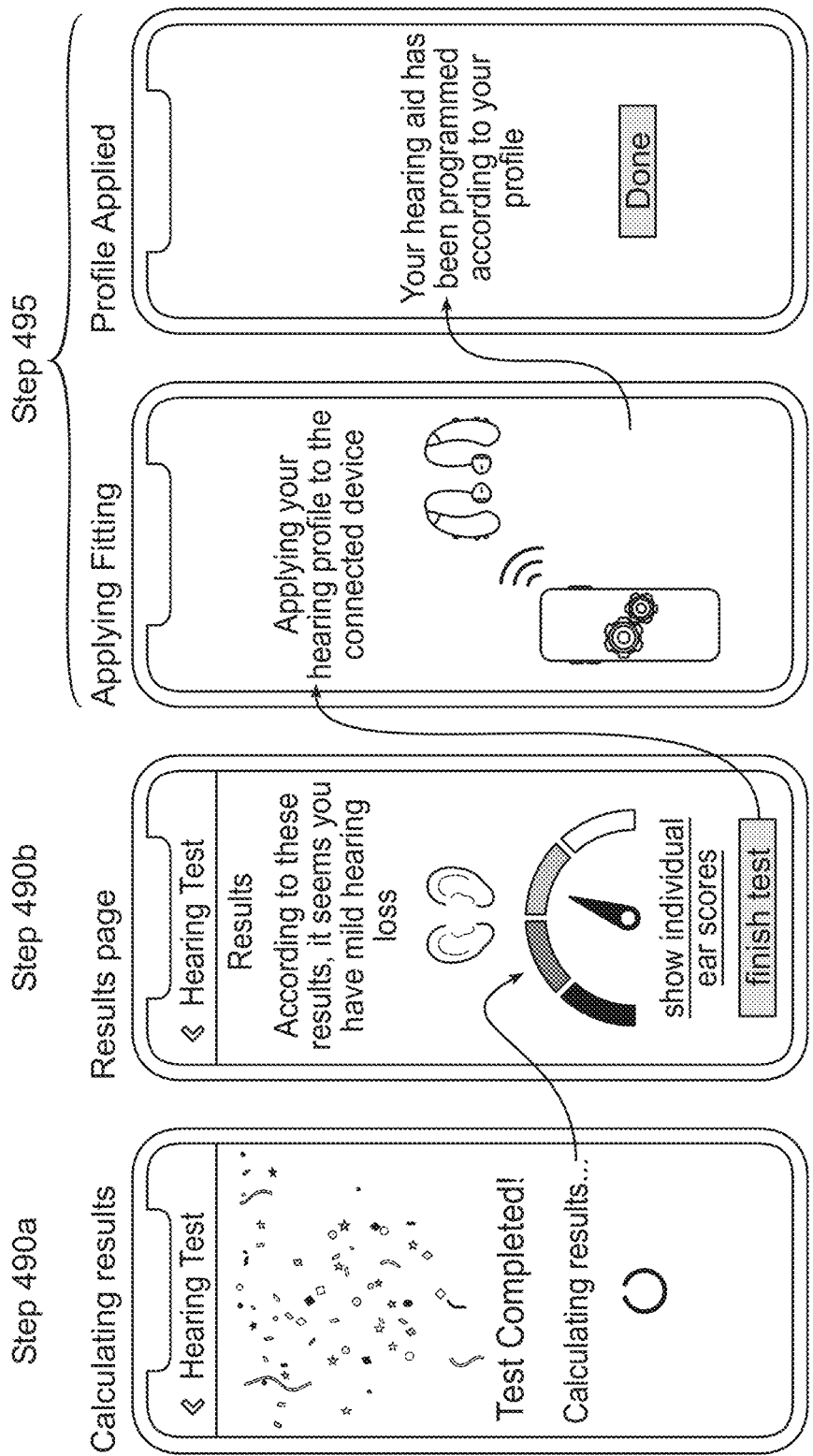

Reference is now made to FIG. 4 which schematically illustrates a flow of the herein disclosed method for automated fitting of a hearing aid, executed using a mobile App, according to some embodiments.

According to some embodiments, the hearing test may include a first step 410 during which a number of questions are posed to the user prior to the test itself. These may include one, some or all (each possibility is a separate embodiment) of the following closed questions and or instructions:

1. Are your family members or friends suggesting you might have hearing loss or that you should take a hearing test? (frequently, occasionally, never).
2. In which ear do you hear better (left, same right).
3. Please connect your hearing aid or headphones to continue.

According to some embodiments, if the user is in possession of a hearing aid, the method may automatically jump to step 480.

According to some embodiments, if the user utilized headphones for the hearing test, the method continues to step 420 at which the user is requested to indicate the type of headphones utilized, as essentially described herein (e.g., whether the headphones are in-ear or over-ear headphones). Then, in step 430a or 430b (depending on headphone type), the user is requested to input whether the headphones are wireless or wired.

In step 440 of the method, the volume of the headphones is increased, and in step 450, a sound check is performed (e.g., the user may be requested to indicate whether a narrator's voice is heard in the right, left or both headphones. Once completed an indication is provided to the user that the hearing test is ready to commence (step 460).

In steps 470a and 470b, which are currently conducted for headphones only, the speech maximum comfortable level (MCL)/thresholds are set, followed by step 480 during which puretones at different frequencies, here 5000 Hz, 1000 Hz, 2000 Hz and 4000 Hz, are tested. Step 480 is conducted for hearing tests performed using headphones as well as for hearing test conducted via a hearing aid.

Steps 470a, 470b and 480 are repeated for each ear.

Upon completion, test results (hearing profile) are calculated and displayed to the user in steps 490a and 490b.

If the user is in possession of hearing aid, the hearing profile may be applied, as shown in step 495.

Figure 5:
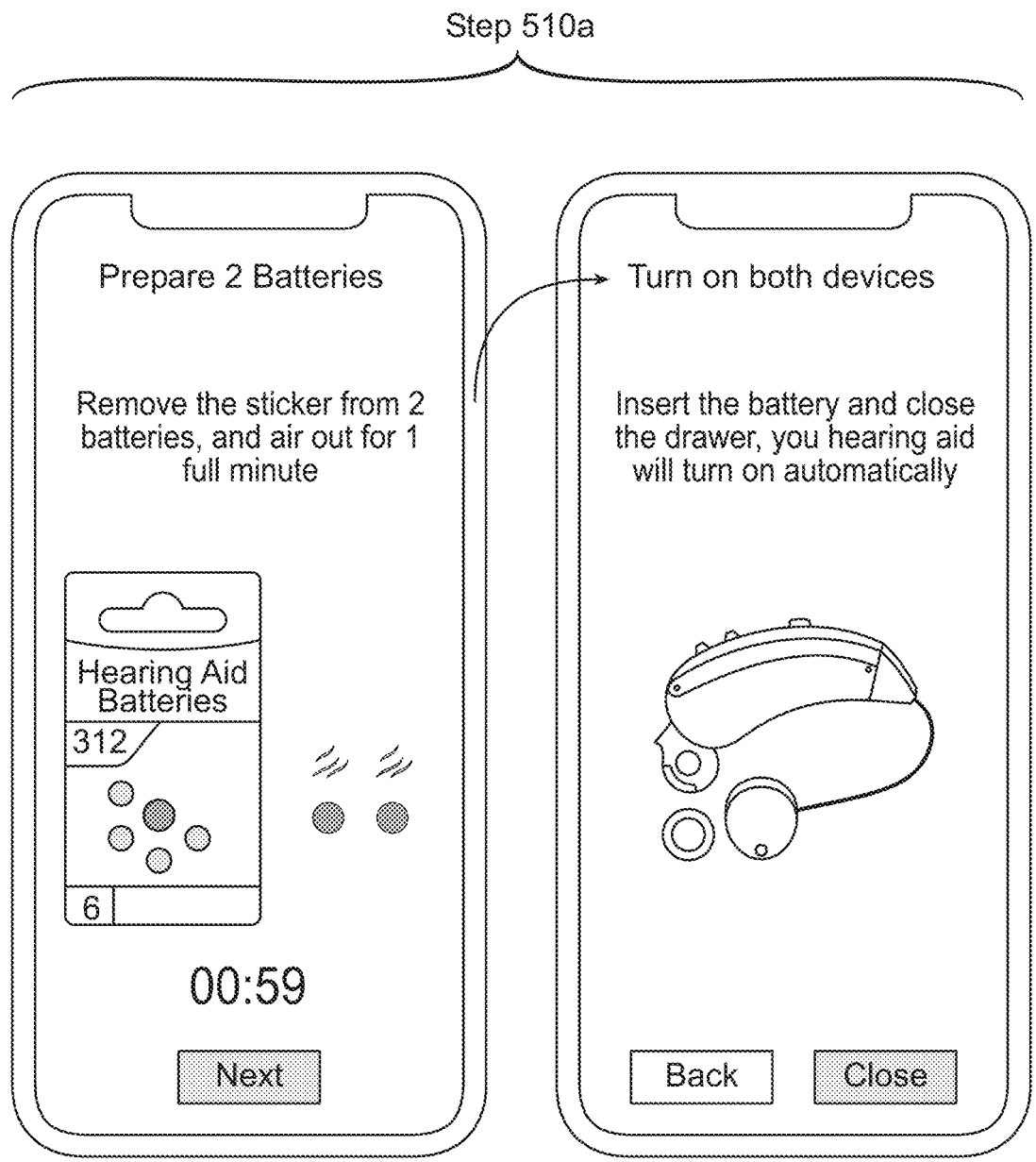
FIG. 5 schematically illustrates the flow of "onboarding" of hearing aids for the herein disclosed method for automated fitting of a hearing aid, executed using a mobile App, according to some embodiments.
Figure 5:
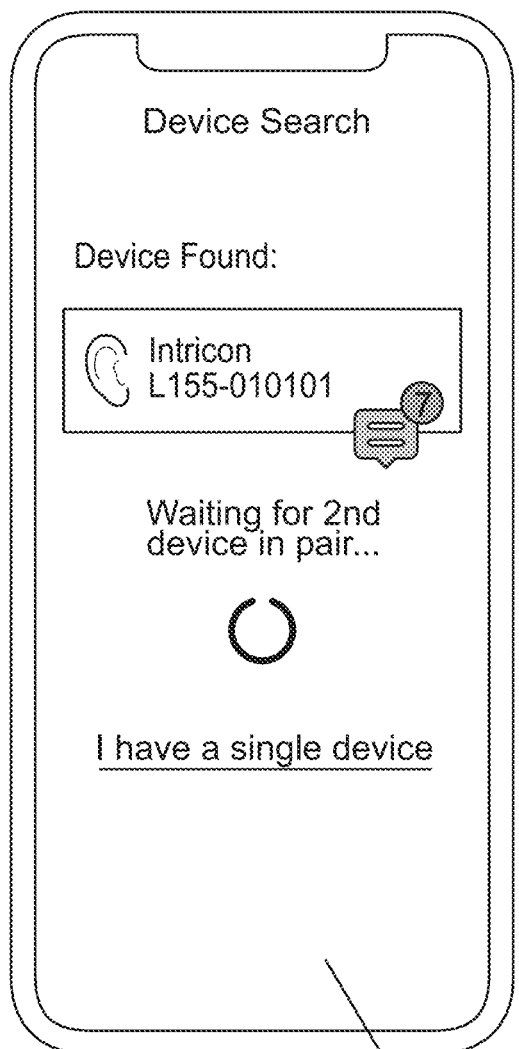
Figure 5:
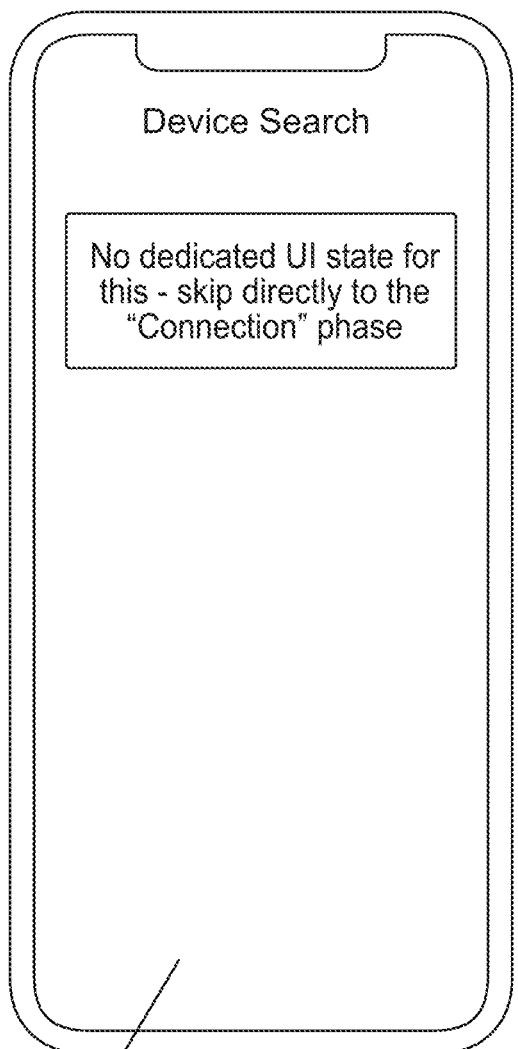
Figure 5:
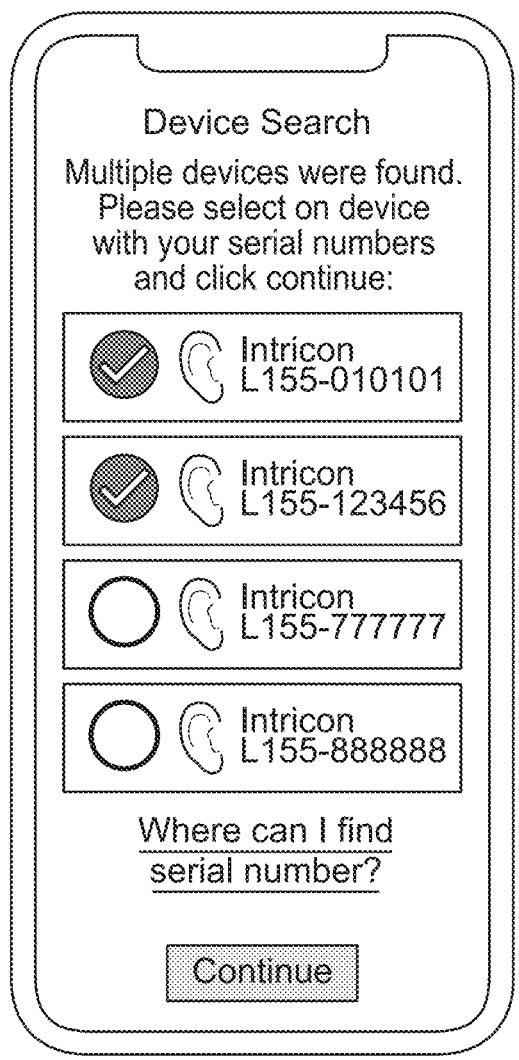
Figure 5:
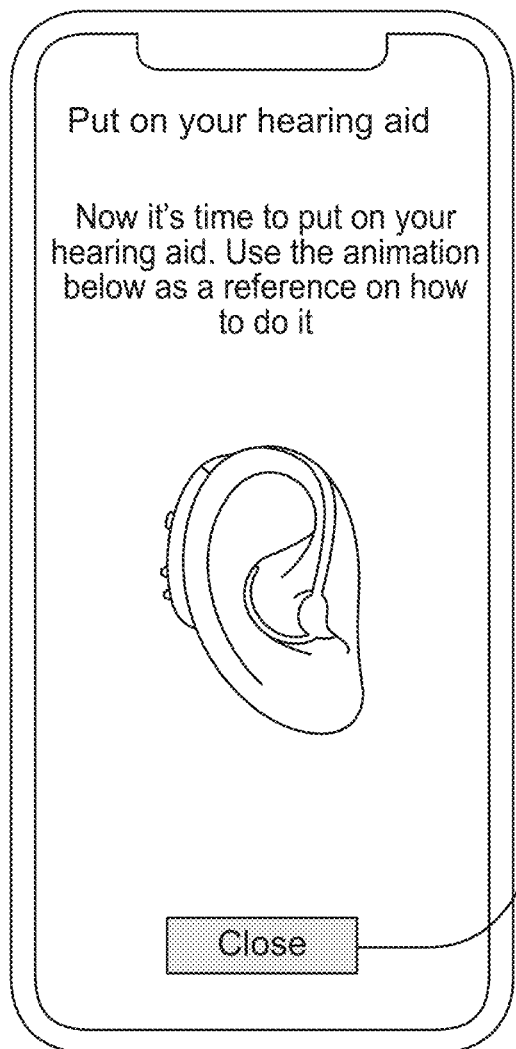
Figure 5:
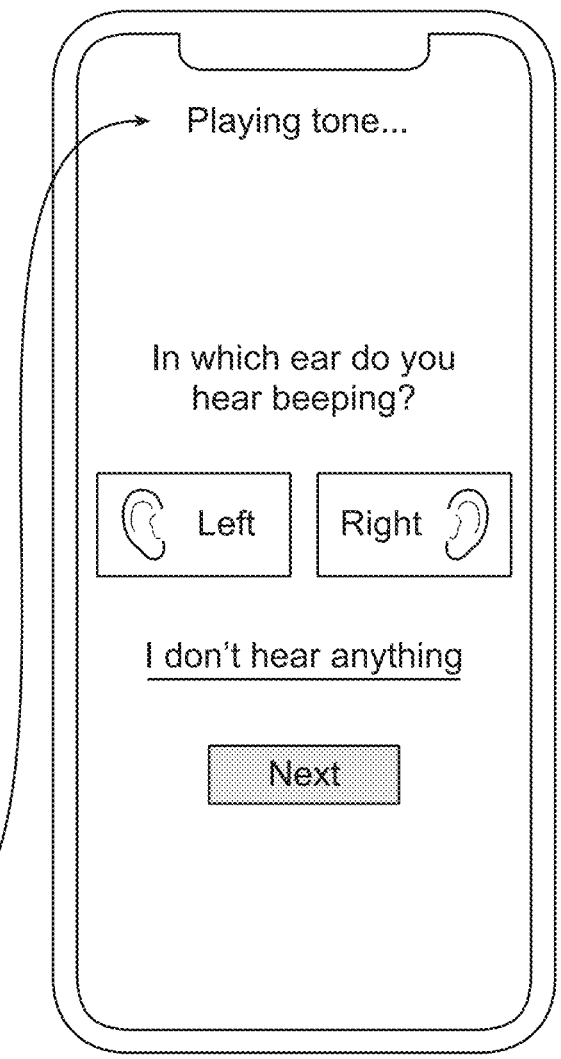
Figure 5:
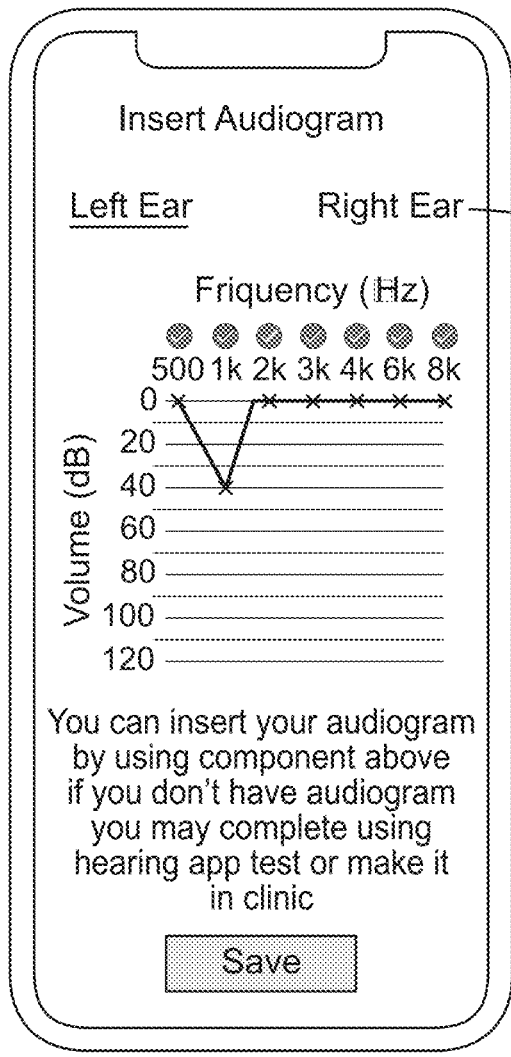
Figure 5:
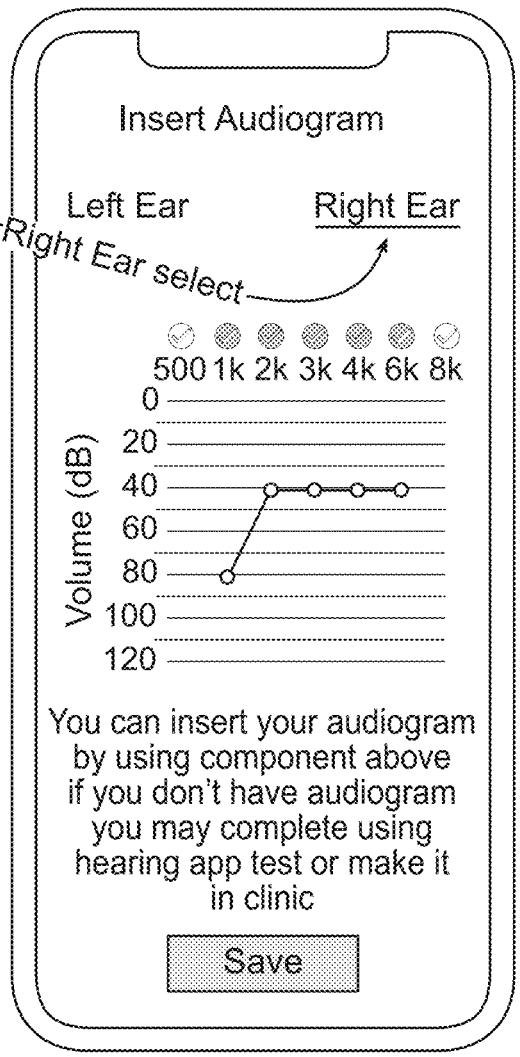

Reference is now made to FIG. 5, which schematically illustrates a flow of the onboarding 500 of hearing aids for herein disclosed method for automated fitting of a hearing aid, executed using a mobile app, according to some embodiments. It is understood by one of ordinary skill in the art, that the onboarding is performed prior to the hearing test (i.e., prior to [but optionally in direct continuation with] the method disclosed with reference to FIG. 4).

The first step of the onboarding an automatic device identification is carried out. The identification may result in 4 optional scenarios:
1) No device is identified. In this case the user may be requested to either confirm that he/she is not in possession of a device or as shown in step 510*a* be requested to activate the device preferably guided by visual instruction;
2) Only one device is located. in which case the user may be requested to confirm that indeed he/she is only in possession of a single hearing aid (step 510*b*),
3) Two hearing devices are identified. In this case the user may automatically be transferred (step 510*c*) to the next step (instructions to put on his/her hearing aid step 520);
4) More than two devices are located. In this case the method may include step 510*d* of automatic sorting of the devices, for example according to signal strength followed by which, the user may be requested to select the right pair.

Once the device has been identified and connected, the user is guided to put on his/her hearing aid (step 520) and a tone is played to ensure correct right/left positioning (step 530) and the hearing test/automated fitting process may commence (as essentially described with regards to FIG. 4).

Alternatively, if the user is already in possession of an audiogram, the method may proceed to upload the audiogram for each ear (steps 540*a* and 540*b*, respectively) and the method of FIG. 4 continued at step 495).

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of automated fitting of a hearing aid, the method comprising:
changing a mode of the hearing aid from a hearing mode to a test mode, wherein the test mode is configured to minimize penetration of external sounds into the hearing aid;
play to the user a recording of speech of one or more individuals with whom the user has frequent interactions,
requesting from the user a feedback regarding the quality hearing the played recording; and
determining a set of hearing aid parameters optimized for hearing the speech of the one or more individuals with whom the user has frequent interactions.

2. The method of claim 1, further comprising automatically recognize the speech of the one or more individuals with whom the user has frequent interactions and to utilize the set of parameters optimized for hearing the speech of the one or more individuals with whom the user has frequent interactions.

3. The method of claim 1, further comprising playing a recording to background noise together with the recording of the speech and to adjusting the set of hearing aid parameters optimized for hearing the speech, based on the feedback regarding the quality of hearing the speech in the background noise.

4. The method of claim 1, wherein the method further comprises a step of uploading the feedback to a cloud, wherein the determining of the suitable set of hearing aid parameters for the hearing aid is performed in the cloud.

5. The method of claim 4, wherein the method further comprises a step of downloading the suitable set of hearing aid parameters from the cloud to the subject's mobile and/or hearing aid.

6. The method of claim 1, wherein the method is executed via the internet or using a dedicated mobile app.

7. The method of claim 6, wherein when the hearing test is executed using the dedicated mobile app, the possession of the hearing aid may be automatically identified.

8. The method of claim 7, further comprising automatically changing a mode of the hearing aid from a test mode to a hearing mode, if a call enters during the hearing test.

9. The method of claim 1, wherein the determining of the suitable set of hearing aid parameters comprises obtaining an external set of recommended hearing aid parameters, and adjusting the external set of recommended hearing aid parameters, based on the feedback.

10. The method of claim 1, wherein the determining of the suitable set of hearing aid parameters comprises obtaining an initial set of recommended hearing aid parameters, the initial set of hearing aid parameters being hearing aid parameters obtained from a subject having a similar user profile.

11. The method of claim 10, wherein the user profile is determined based on at least two parameters selected from, age, gender, years of hearing deficiency, source of hearing deficiency, previous hearing aid usage, interests/hobbies, occupation.

12. The method of claim 10, wherein the similar user profile is chosen by the user.

13. A system for automated fitting of a hearing aid, the system comprising a processing logic configured to:
change a mode of the hearing aid from a hearing mode to a test mode, wherein the test mode is configured to minimize penetration of external sounds into the hearing aid;
play to the user a recording of speech of one or more individuals with whom the user has frequent interactions,
requesting from the user a feedback regarding the quality hearing the played recording; and
determining a set of hearing aid parameters optimized for hearing the speech of the one or more individuals with whom the user has frequent interactions.

14. The system of claim 13, wherein the processing logic is further configured to automatically recognize the speech of the one or more individuals with whom the user has frequent interactions and to utilize the set of parameters optimized for hearing the speech of the one or more individuals with whom the user has frequent interactions.

15. The system of claim 13, wherein the processing logic is further configured for playing a recording to background noise together with the recording of the speech and to adjusting the set of hearing aid parameters optimized for hearing the speech, based on the feedback regarding the quality of hearing the speech in the background noise.

16. The system of claim 13, wherein the processing logic is further configured to receive an indication regarding the type of hearing device utilized for the hearing test, wherein, in case the user is not in possession of a hearing aid, the processing logic is configured to trigger a request to the user to utilize headphones.

17. The system of claim 16, wherein the requesting of the user to utilize headphones comprises requesting the user to provide at least one feature of the headphone, wherein the at least one feature is selected from: closed/open back, on-ear/over-ear/in ear/ear-buds, wired/wireless, noise-cancelling, brand or any combination thereof.

* * * * *